United States Patent
Ondrus et al.

(10) Patent No.: US 10,793,496 B2
(45) Date of Patent: Oct. 6, 2020

(54) PROCESS FOR PRODUCING A CHLORINATED ALKANE

(71) Applicant: SPOLEK PRO CHEMICKOU A HUTNI VYROBU A.S., Usti nad Labem (CZ)

(72) Inventors: Zdenek Ondrus, Vrbice (CZ); Pavel Kubicek, Decin (CZ)

(73) Assignee: SPOLEK PRO CHEMICKOU A HUTNI VYROBU A.S., Utsi nad Labem (CZ)

( * ) Notice: Subject to any disclaimer, the term of this patent is extended or adjusted under 35 U.S.C. 154(b) by 0 days.

(21) Appl. No.: 16/092,451

(22) PCT Filed: Apr. 12, 2017

(86) PCT No.: PCT/CZ2017/000024
§ 371 (c)(1),
(2) Date: Oct. 10, 2018

(87) PCT Pub. No.: WO2017/177988
PCT Pub. Date: Oct. 19, 2017

(65) Prior Publication Data
US 2019/0185395 A1 Jun. 20, 2019

(30) Foreign Application Priority Data
Apr. 13, 2016 (CZ) .................................. 2016-214

(51) Int. Cl.
| | | |
|---|---|---|
| *C07C 17/04* | (2006.01) | |
| *C07C 17/013* | (2006.01) | |
| *C07C 17/06* | (2006.01) | |
| *C07C 17/093* | (2006.01) | |
| *C07C 17/10* | (2006.01) | |
| *C07C 19/01* | (2006.01) | |

(52) U.S. Cl.
CPC ............ *C07C 17/04* (2013.01); *C07C 17/013* (2013.01); *C07C 17/06* (2013.01); *C07C 17/093* (2013.01); *C07C 17/10* (2013.01)

(58) Field of Classification Search
CPC ....... C07C 17/013; C07C 17/02; C07C 17/04; C07C 17/06; C07C 17/093; C07C 17/10
See application file for complete search history.

(56) References Cited

U.S. PATENT DOCUMENTS

| | | | |
|---|---|---|---|
| 2,420,801 A | 5/1947 | Stratton | |
| 3,932,544 A | 1/1976 | Lovelace | |
| 4,301,314 A * | 11/1981 | Rideout | .................. C07C 17/10 570/253 |
| 4,614,572 A * | 9/1986 | Holbrook | ............... B01J 19/123 204/157.95 |
| 6,551,469 B1 * | 4/2003 | Nair | ........................ C07C 17/10 204/157.95 |
| 8,252,964 B2 | 8/2012 | Devic et al. | |
| 2010/0331583 A1 | 12/2010 | Johnson et al. | |
| 2012/0053374 A1 | 3/2012 | Fukuju et al. | |
| 2012/0157723 A1 | 6/2012 | Fukuju et al. | |
| 2014/0235903 A1 | 8/2014 | Wang et al. | |
| 2014/0235906 A1 | 8/2014 | Yang et al. | |
| 2017/0050904 A1 * | 2/2017 | Ondrus | ................. C07C 17/383 |

FOREIGN PATENT DOCUMENTS

| | | |
|---|---|---|
| KR | 100686200 | 2/2007 |
| WO | WO 2009/085862 | 9/2009 |
| WO | WO 2013/015068 | 1/2013 |
| WO | WO 2013/055894 | 4/2013 |
| WO | WO 2013/086262 | 6/2013 |
| WO | WO 2013/119919 | 8/2013 |
| WO | WO 2013/184865 | 12/2013 |
| WO | WO 2014/116562 | 7/2014 |
| WO | WO 2014/164368 | 10/2014 |
| WO | PCT/CZ2015/000122 | 4/2016 |
| WO | WO 2016/058566 | 4/2016 |
| WO | WO 2017/028826 | 8/2016 |

OTHER PUBLICATIONS

KR100686200-translation, Feb. 15, 2007, pp. 1-4 (Year: 2007).*

* cited by examiner

*Primary Examiner* — Medhanit W Bahta
(74) *Attorney, Agent, or Firm* — Pearl Cohen Zedek Latzer Baratz LLP

(57) ABSTRACT

A process for producing a chlorinated alkane in which an alkene or an alkane feedstock is contacted with chlorine in a chlorination zone to produce a reaction mixture containing the chlorinated alkane, wherein the chlorine supplied into the chlorination zone has an oxygen content of less than about 2000 ppmv and wherein: the chlorination zone is closed to the atmosphere, and/or the chlorination zone is operated under atmospheric or superatmospheric pressure, and/or the chlorination zone is operated under an inert atmosphere, and/or the content of dissolved oxygen in the alkene or alkane feedstock is less than 2000 ppm.

15 Claims, No Drawings

PROCESS FOR PRODUCING A CHLORINATED ALKANE

CROSS-REFERENCE TO RELATED APPLICATIONS

This application is a National Phase Application of PCT International Application No. PCT/CZ2017/000024, international filing date Apr. 12, 2017, claiming the benefit of Czech Provisional Patent Application No. PV2016-214, filed Apr. 13, 2016, all of which is hereby incorporated by reference.

The present invention relates to processes for producing chlorinated alkane compounds having acceptably low levels of oxygenated impurities.

Haloalkanes find utility in a range of applications. For example, halocarbons are used extensively as refrigerants, blowing agents and foaming agents. Throughout the second half of the twentieth century, the use of chlorofluoroalkanes increased exponentially until the 1980's, when concerns were raised about their environmental impact, specifically regarding depletion of the ozone layer.

Subsequently, fluorinated hydrocarbons such as perfluorocarbons and hydrofluorocarbons have been used in place of chlorofluoroalkanes, although more recently, environmental concerns about the use of that class of compounds have been raised and legislation has been enacted in the EU and elsewhere to reduce their use.

New classes of environmentally friendly halocarbons are emerging and have been investigated, and in some cases, embraced in a number of applications, especially as refrigerants in the automotive and domestic fields. Examples of such compounds include hydrofluoroolefins (HFOs) such as 2-chloro-3,3,3-trifluoropropene (HCFO-1233xf), 1,3,3,3-tetrafluoropropene (HFO-1234ze), 3,3,3-trifluoropropene (HFO-1243zf); and 2,3,3,3-tetrafluoropropene (HFO-1234yf), 1,2,3,3,3-pentafluoropropene (HFO-1225ye), 1-chloro-3,3,3-trifluoropropene (HCFO-1233zd), 3,3,4,4,4-pentafluorobutene (HFO-1345zf), 1,1,1,4,4,4-hexafluorobutene (HFO-1336mzz), 3,3,4,4,5,5,5-heptafluoropentene (HFO-1447fz), 2,4,4,4-tetrafluorobut-1-ene (HFO-1354mfy) and 1,1,1,4,4,5,5,5-octafluoropentene (HFO-1438mzz).

While these compounds are, relatively speaking, chemically non-complex, their synthesis on an industrial scale to the required levels of purity is challenging.

Attempts to prevent or retard the formation of unwanted impurities in HFO production are disclosed in the prior art. For example, US2010/331583 and WO2013/119919 describe the need for purity in the part fluorinated feedstock (as well as approaches for improving purity). Additionally, U.S. Pat. No. 8,252,964 describes use of molecular sieves to remove impurities from HFO compounds. WO2013/184865 advocates the use of further reactions to separate out difficult to remove impurities from HFO compounds of interest. US2014/235903 addresses the problem of reactor impurities.

Chlorinated starting materials are of growing importance as feedstocks for the manufacture of HFO compounds. One factor which may influence the formation of unwanted impurities is the purity and impurity profile of the chlorinated starting materials as this will have a substantial effect on the success and viability of downstream processes (especially continuous processes) for preparing the desirable fluorinated HFO products. The presence of certain impurities will result in side reactions, minimising the yield of the target compound. Impurities in the chlorinated feedstock may also be transformed into fluorinated impurities in the HFO compound of interest. Removal of these impurities through the use of distillation steps is also challenging and/or inefficient. Additionally, the presence of certain impurities will compromise catalyst life, by, for example, acting as catalyst poisons.

A variety of impurities are known in the art to exist in commercially available chlorinated alkane feedstocks, e.g. chlorinated alkanes other than the compound of interest, under chlorinated compounds (i.e. compounds comprising fewer chlorine atoms than the compound of interest), over chlorinated compounds (i.e. compounds comprising more chlorine atoms than the compound of interest), isomers of the target compound, and/or residues of any catalysts used.

Specific examples of such compounds and processes for minimising their formation have been proposed in the art.

For example, WO2013/086262 discloses a process for preparing 1,1,2,2,3-pentachloropropane from methylacetylene gas.

WO2013/055894 discloses a process for producing tetrachloropropenes, particularly 1,1,2,3-tetrachloropropene and reports that the product obtained from the processes disclosed in that document have advantageously low levels of impurities which can be problematic in downstream processes for producing fluorocarbons. A discussion of the different types of impurities considered to be problematic by the authors of WO2013/055894 is set out in paragraphs [0016] and [0017] of that document.

US2012/157723 discloses a process in for preparing chlorinated alkanes via a three step process.

Additional processes in which processes are streamlined by using crude intermediates in downstream stages are disclosed in WO2009/085862.

However, there is limited disclosure in the prior art regarding which of these impurities are particularly problematic and which impurities may be tolerated. The present inventors now understand that one specific class of impurities is especially problematic in downstream reactions (for example, hydrofluorination reactions resulting in the preparation of chlorofluorinated or the fluorinated final compounds of interest) namely oxygenated organic compounds. These compounds can destabilize chlorinated alkane feedstocks upon storage or transport. Further, their presence in chlorinated alkane feedstocks can result in the formation of large quantities of downstream impurities which reduces the yield of the HFO compound of interest.

To the inventors' knowledge, this class of impurities has not been previously identified as problematic, nor have there been any disclosures or teachings focussed on minimising or eliminating these impurities during the production of chlorinated alkane compounds.

In view of this understanding that the presence of oxygenated impurities in chlorinated alkane feedstocks can render downstream processes non-viable or at the least, highly challenging, a demand exists for chlorinated alkane compounds comprising acceptably low levels of oxygenated impurities and also for efficient and reliable processes for preparing such materials.

The inventors found through exhaustive studies that surprisingly chlorine facilitates the formation of oxygenated compounds when chlorinated alkenes or alkanes are reacted with chlorine and sources of oxygen are present.

Thus, according to a first aspect of the present invention, there is provided a process for producing a chlorinated alkane in which an alkene or alkane feedstock is contacted with chlorine in a chlorination zone to produce a reaction mixture containing the chlorinated alkane, wherein the chlorine supplied into the chlorination zone has an oxygen content of less than about 2000 ppmv and wherein the chlorination zone is closed to the atmosphere, and/or the chlorination zone is operated under atmospheric or super-atmospheric pressure, and/or the chlorination zone is operated under an inert atmosphere, and/or the content of dissolved oxygen in the alkene feedstock is less than 2000 ppm.

As demonstrated by the accompanying examples, the inventors have identified that the formation of oxygenated organic impurities in chlorination reactions can be minimised through the use of chlorine having low oxygen levels.

Thus, according to another aspect of the present invention, there is provided a process for minimising the formation of oxygenated chlorinated compounds when producing a chlorinated alkane in which an alkene or alkane feedstock is contacted with chlorine in a chlorination zone to produce a reaction mixture containing the chlorinated alkane, wherein the chlorine supplied into the chlorination zone has an oxygen content of less than about 2000 ppmv and wherein:
  the chlorination zone is closed to the atmosphere, and/or
  the chlorination zone is operated under atmospheric or superatmospheric pressure, and/or
  the chlorination zone is operated under an inert atmosphere, and/or the content of dissolved oxygen in the alkene feedstock is less than 2000 ppm.

Although commercial sources of chlorine comprising low levels of oxygen exist, the skilled addressee will recognise that those chlorine sources are significantly more costly than conventionally employed chlorine gas sources (which typically comprise oxygen at levels of around 0.5 to 2.0%) such as those obtained from chlor-alkali membrane or diaphragm electrolysis plants and would not have employed them on an industrial scale without justification.

U.S. Pat. No. 3,932,544 mentions chlorination at controlled rate of chlorine feed to avoid heavies, and the mention of purging of oxygen. There is no mention of removing oxygen from the chlorine feed itself.

KR100686200 describes a process where oxygen is removed from chlorine, and this chlorine is used in e.g. production processes of chloroform, carbon tetrachloride.

As used herein, the term 'oxygenated organic impurities' or 'oxygenated organic compounds' means compounds comprising carbon, hydrogen and oxygen atoms. Examples of oxygenated organic compounds include chlorinated alcohols, chlorinated alkanols, chlorinated acid chlorides, chlorinated carboxylic acids, chlorinated aldehydes, chlorinated ketones, chlorinated peroxides.

Examples of $C_3$ oxygenated organic impurities include propanol or propanoyl compounds, while examples of $C_2$ oxygenated organic impurities include ethanol or ethanoyl compounds. An example of $C_1$ oxygenated organic impurities includes phosgene.

These compounds are of particular concern as they are generally difficult to separate from chlorinated alkanes using conventional techniques such as distillation. Other problems which arise from the presence of these compounds are discussed herein.

The reaction mixture produced in the chlorination zone may be extracted therefrom and optionally be subjected to additional treatment steps, discussed in detail below.

In embodiments of the invention, the content of oxygenated organic compounds in reaction mixture extracted from the chlorination zone is about 2000 ppm or less, about 1000 ppm or less, about 500 ppm or less, about 200 ppm or less, about 150 ppm or less, about 100 ppm or less, about 50 ppm or less, about 20 ppm or less or about 10 ppm or less, or about 5 ppm or less.

The composition of reaction mixture, enabling a determination of the content of oxygenated organic compounds, may be determined as soon as is practicable following extraction of the reaction mixture from the chlorination zone. For example, a sample of reaction mixture may be extracted at a point adjacent to or slightly downstream of the outlet of the chlorination zone.

Reaction mixture may be extracted from the chlorination zone either continuously or intermittently. One skilled in the art will recognise that, in embodiments where reaction mixture is extracted from the chlorination zone, that material may be removed on a substantially continuous basis while the chlorination zone is at operating conditions and, if its purpose is to set up a steady state reaction, once the reaction mixture therein has attained the required steady state.

In embodiments of the present invention, the reaction conducted in the chlorination zone is in the liquid phase, i.e., the reaction mixture present therein is predominantly or totally liquid. The reaction mixture may be analysed using any techniques known to those skilled in the art e.g. chromatography.

As mentioned above, the chlorine employed in the processes of the present invention comprises an oxygen ($O_2$) content of about 2000 ppmv or less. Use of chlorine comprising such low levels of oxygen advantageously minimises the formation of problematic oxygenated organic compounds, especially oxygenated chlorinated compounds. In embodiments of the invention, the chlorine fed into the chlorination zone may comprise about 1500 ppmv or less, about 1000 ppmv or less, about 500 ppmv or less, about 250 ppmv or less, about 150 ppmv or less, about 100 ppmv or less, about 50 ppmv or less, about 20 ppmv or less or about 10 ppmv or less of oxygen.

In embodiments of the invention, the chlorine supplied to the chlorination zone is gaseous.

Commercially available sources of chlorine comprising low levels of oxygen are available. However, chlorine sources comprising such low levels of oxygen are more costly than conventionally employed chlorine sources. To minimise operating cost, and also to provide the user of the process with greater control over the oxygen content of the chlorine starting material, in embodiments of the invention, a commercially available source of chlorine having a higher oxygen content than that fed into the chlorination zone may be firstly treated to reduce its oxygen content. Alternatively, if technically feasible, low oxygen-content chlorine gas may be produced, for example by the membrane or diaphragm electrolysis of hydrochloric acid.

KR100686200 describes a process where oxygen is removed from chlorine, and this chlorine is used in e.g. production processes of chloroform, carbon tetrachloride.

The skilled reader will be familiar with techniques and apparatus to reduce the content of oxygen in chlorine sources. For example, oxygen can be removed from a chlorine source through the use of a liquefying unit in which the chlorine gas feedstock is partially liquefied using a combination of appropriate temperatures and pressures. The chlorine which is liquefied has a low oxygen content and can be evaporated to produce a low oxygen-content chlorine gas feedstock. While such approaches are costly and the storage of liquefied chlorine is hazardous, in view of the inventors' finding of the importance of minimising the oxygen content of chlorine sources used in the production of chlorinated alkanes, the burden of minimising oxygen content in the chlorine source is justified.

The chlorine used as a starting material in the processes of the present invention is preferably highly pure. In embodiments of the invention, the chlorine fed into the chlorination zone preferably has a purity of at least about 95% vol, at least about 97% vol, at least about 99% vol, at least about 99.5% vol, at least about 99.8% vol, or at least about 99.9% vol.

Additionally or alternatively, the chlorine used in the processes of the present invention may comprise water in an amount of about 200 ppmv or less, about 100 ppmv or less, about 50 ppmv or less, about 20 ppmv or less or about 10 ppmv or less.

Chlorine may be fed into the chlorination zone in liquid and/or gaseous form, either continuously or intermittently. For example, the chlorination zone may be fed with one or more chlorine feeds.

Where the reaction mixture in the chlorination zone is liquid, the chlorine may be fed into the chlorination zone as gas and dissolved in the chlorination zone.

In embodiments, the chlorine is fed into chlorination zone via dispersing devices, for example, nozzles, porous plates, tubes, ejectors, etc. The chlorine, in embodiments of the invention, may be fed directly into the liquid reaction mixture. Additionally or alternatively, the chlorine may be fed into liquid feeds of other reactants upstream of the chlorination zone.

Additional vigorous stirring may be used to ensure good mixing and/or dissolution of the chlorine into the liquid reaction mixture. As those skilled in the art will recognise, steps to minimise the ingress of oxygen (or sources thereof, such as air) and/or water into the chlorination apparatus should be taken.

The alkene used in the processes of the present invention may be a $C_{2-6}$ alkene, for example, an ethene (i.e. a $C_2$ alkene), a propene, a butene, a pentene or a hexene.

The alkene may or may not be halogenated, e.g. chlorinated, brominated and/or iodinated. Further, the alkene may be straight-chain or branched, cyclic and/or substituted. In arrangements in which the alkene is chlorinated, it preferably comprises 1, 2, 3, 4 or 5 chlorine atoms.

Examples of alkene materials that may be employed in the processes of the present invention include ethene, chloroethene, chloropropene, chlorobutene, vinyl chloride, propene, 2-chloropropene, 3-chloropropene, 2,3,3,3-Tetrachloropropene, 1,1-dichloroethene, trichloroethene, chlorofluoroethene, 1,2-dichloroethene, 1,1-dichloro-difluoroethene, 1-chloropropene, 1-chlorobutene, 1,1,3-trichloropropene, 1,1,2-trichloropropene, 2,3,3-trichloropropene, 1,1,4,4,4-pentachlorobutene, 3,3,3-trichloropropene, 1,2,3-trichloropropene, 1,3-dichloropropene, 1,1-dichloropropene, 1,1,2,3-tetrachloropropene, 1,1,3,3-tetrachloropropene, 1,1,2,3,3-pentachloropropene, 1,1,3,3,3-pentachloropropene and 1,1,2,3,3,3-hexachloropropene and/or any of the other alkenes disclosed in U.S. Pat. No. 5,902,914, the contents of which are incorporate by reference.

Chlorinated propenes, butenes, pentenes or hexenes may be employed in the processes of the present invention to produce chlorinated $C_{3-6}$ compounds which are of interest and find utility in the production of fluorinated compounds having low global warming potential.

The alkene or alkane used as a starting material in the processes of the present invention preferably has a high degree of purity. In embodiments of the invention, the alkene has a purity level of at least about 95%, at least about 97%, at least about 99%, or at least about 99.5%.

Additionally or alternatively, the alkene or alkane may include less than about 2%, less than about 1%, less than about 0.1%, less than about 0.01% or less than about 0.001% by weight of alkene and/or alkane impurities. For example, where the chlorinated alkene starting material is 1,1,3-trichloropropene, the 1,1,3-trichloropropene starting material may comprise less than about 2%, less than about 1%, less than about 0.1%, less than about 0.01% or less than about 0.001% by weight of chlorinated alkene impurities such as 3,3,3-trichloropropene and/or tetrachloroethylene and/or chlorinated alkane impurities such as 1,1,1,3-tetrachloropropane.

Processes for producing high purity chlorinated alkene are disclosed in WO 2016/058567, the contents of which are incorporated herein by reference. Products of those processes may advantageously comprise:

about 95% or more, about 97% or more, about 99% or more, about 99.2% or more about 99.5% or more or about 99.7% or more of the chlorinated alkene, less than about 1000 ppm, less than about 500 ppm, less than about 200 ppm, or less than about 100 ppm of chlorinated $C_{5-6}$ alkane impurities, less than about 1000 ppm, less than about 500 ppm, less than about 200 ppm, or less than about 100 ppm of chlorinated alkene impurities (i.e. chlorinated alkenes other than the starting material), less than about 500 ppm, less than about 200 ppm, less than about 100 ppm, less than about 50 ppm, less than about 20 ppm, less than about 10 ppm or less than about 5 ppm metal (e.g. iron), less than about 1000 ppm, less than about 500 ppm, less than about 250 ppm, or less than about 100 ppm of oxygenated organic compounds, and/or less than about 500 ppm, about 250 ppm or less, about 100 ppm or less, about 50 ppm or less, about 20 ppm or less or about 10 ppm or less of water.

For the avoidance of doubt, the limits of metal outlined above encompass metal in elemental form (e.g. particulate metal) as well as in ionic form (e.g. in the form of a salt).

The alkene material used as a starting material in the processes of the present invention may be provided in a composition having the impurity profile as outlined above.

The alkene material used as a feedstock in the processes of the present invention additionally may comprise dissolved oxygen in an amount of less than about 2000 ppm, about 1000 ppm or less, about 500 ppm or less, about 200 ppm or less, about 150 ppm or less, about 100 ppm or less, about 50 ppm or less, about 20 ppm, about 10 ppm or less, about 5 ppm or less or about 2 ppm or less.

The chlorinated alkene employed in the processes of the present invention may be fed into the chlorination zone using any technique known to those skilled in the art. As those skilled in the art will recognise, steps to minimise the ingress of oxygen (or sources thereof, such as air) and/or moisture into the chlorination apparatus should be taken.

The skilled reader will be familiar with techniques and apparatus which permit chlorinated alkanes to be obtained from alkene starting materials via chlorination reactions. Additional assistance is also provided herein. Using such processes, a broad range of chlorinated alkanes can be prepared. Examples of such processes are disclosed in PCT/CZ2015/000122, US2012/053374, US2014/235906 and WO2013/015068, the contents of which are incorporated by reference.

The invention is also applicable to the chlorination of a chlorinated alkane to produce a higher chlorinated alkane. It is believed that the chlorination of the chlorinated alkane starting material proceeds via an intermediate, which is then in situ chlorinated to form the higher chlorinated alkane product. This intermediate appears susceptible to react with oxygen. Thus, chlorine and controlled reactor conditions to ensure very low oxygen content is believed to be important. For example the starting chlorinated alkane is 1,1,1,3-tetrachloropropane which is chlorinated with chlorine in the presence of applied UV, and/or a catalyst, for example a metal salt, to produce 1,1,1,2,3-pentachloropropane. The metal salt may be for example ionic metal compounds such as Lewis acids from transition or post-transition metals.

Example processes for such chlorination of a chlorinated alkane to another chlorinated alkane, via an in situ produced intermediate, for example a chlorinated alkene, may be be as described in WO2017028826, WO2009085862, WO2014116562, WO2014164368. The alkane starting material to use herein is described, for example, in WO2016058566.

In embodiments, radical and/or ionic chlorination may be employed. As those skilled in the art will recognise, ionic chlorination typically requires some form of catalyst to be used (for example, ionic metal compounds such as Lewis acids from transition or post-transition metals) which advantageously enables the reaction to proceed at lower temperatures while achieving good yield and product purity. Radical chlorination typically involves the application of electromagnetic irradiation (e.g. the application of UV and/or visible light) or heat.

In embodiments of the invention, the chlorinated alkane produced may be a $C_{2-6}$ chloroalkane, for example, chloroethane, chloropropane or chlorobutane, or a $C_{3-6}$ chloroalkane. Examples of chlorinated alkanes which may be produced in the processes of the invention include 1,1,1,2,3-pentachloropropane, 1,1,1,3,3-pentachloropropane, 1,1,2,3-tetrachloropropane, 1,1,2,2,3-pentachloropropane, 1,1,1,2,2-pentachloropropane, 1,1,1,2,4,4,4-heptachlorobutane, 1,1,1,2,3,3-hexachloropropane, 1,1,1,2,3,3,3-heptachloropropane, 1,1,1,2,2,3,3-heptachloropropane and 1,1,1,2,2,3,3,3-octachloropropane.

Any conditions which result in the chlorination of the alkene or alkane starting material to form the chlorinated alkane of interest may be employed in the chlorination zone. However, in embodiments of the invention, the operating temperature in the chlorination zone may be maintained at a relatively low level, for example about 100° C. or lower, about 90° C. or lower or about 80° C. or lower. The operating temperature of the chlorination zone may be about −30° C. to about 75° C., about −20° C. to about 40° C., about −10° C. to about 30° C. or about 0° C. to about 20° C. The use of such temperatures in the chlorination zone has been found to be unexpectedly advantageous as this results in a reduction in the formation of isomers of the target chlorinated alkane, yet gives the required product selectively in high yield. To increase the reaction rate at these temperatures, light (visible and/or ultra violet) may optionally be used to promote the addition of chlorine.

In embodiments of the invention, the molar ratio of chlorine:alkene or chlorine:alkane feedstock may range from about 0.3:1.0 or about 0.5:1.0 to about 1.1:1.0, or about 1.5:1.0. In specific embodiments, the chlorine provided to the chlorination zone may be controlled to ensure that a stoichiometric excess of alkene or alkane feedstock is present. For example, the molar ratio of chlorine:alkene or chlorine:alkane in the reaction mixture in the chlorination zone may be <1:1, may be ≤0.95:1, may be ≤0.9:1, may be ≤0.85:1, may be ≤0.8:1, may be ≤0.5:1, or may be ≤0.3:1 or less. Such control of the chlorine content in the reaction mixture facilitates more controlled chlorination reactions in embodiments of the invention (particularly in those where the chlorination zone is operated on a continuous basis) and this can inhibit the excessive formation of oxygenated chlorinated side products.

The operating temperature in the chlorination zone may be controlled by any temperature control means known to those skilled in the art, for example heating/cooling jackets, heating/cooling loops either internal or external to the reactor, heat exchangers and the like. Additionally or alternatively, the temperature may be controlled by controlling the temperature of material/s added into the reaction mixture, thus, controlling the temperature of the reaction mixture. The reaction mixture is maintained in the chlorination zone for a time and under conditions sufficient to achieve the required level of chlorination.

In embodiments of the invention, the chlorination zone is exposed to light, for example visible light and/or ultra violet light. Exposure of the reaction mixture to light promotes the reaction when operated at low temperatures which is advantageous where the use of higher temperature is to be avoided.

In embodiments of the present invention, the residence time of the reaction mixture in the chlorination zone may range from about 30 to 300 minutes, from about 40 to about 120 minutes or from about 60 to about 90 minutes.

Any type of reactor known to those skilled in the art may be employed in the processes of the present invention. Specific examples of reactors that may be used to provide chlorination zone are column reactors (e.g. column gas-liquid reactors), tubular reactors (e.g. tubular gas phase reactors), bubble column reactions, plug/flow reactors and stirred tank reactors, for example continuously stirred tank reactors.

In embodiments of the invention, a plurality of chlorination zones may be employed. These may be provided in sequence. In embodiments in which a plurality of chlorination zones, these may be provided in reactors of the same or different type. For example, the chlorination zones may be provided by a plurality of continuously stirred tank reactors operated in sequence.

Alternatively, a first chlorination zone may be provided in a first reactor optionally selected from those identified in the preceding paragraph, and a second chlorination zone may be provided in a second reactor which differs from the first reactor type which is optionally selected from those identified in the preceding paragraph. For example, the first reactor may be a continuously stirred tank reactor and the second reactor may be a plug/flow reactor.

In embodiments of the invention, the chlorination zone is closed to the atmosphere. In other words, during operation of the chlorination zone, it is not in fluid communication with the external environment and is configured to prevent the ingress of oxygen (e.g. in the air) and/or moisture.

Reactors used in the processes of the present invention may be divided into different zones each having different flow patterns and/or different operating temperatures/pressures. For example, chlorination may be performed in a reactor including a plurality of reaction zones. Those zones may be operated at different temperatures and/or pressures.

Additionally or alternatively, reactors used in the processes of the present invention may be provided with external circulation loops. The external circulation loops may optionally be provided with cooling and/or heating means.

As those skilled in the art will recognise, chlorination zones can be maintained at differing temperatures through use of cooling/heating elements such as cooling tubes, cooling jackets, cooling spirals, heat exchangers, heating fans, heating jackets or the like.

The skilled reader will also appreciate that such apparatus, especially in systems which are operated on a continuous basis, will comprise conduits (e.g. pipes) to carry starting materials, reaction mixture and other materials. In embodiments of the invention, the connections between these conduits and other components of the system may be configured to minimise the ingress of moisture and/or oxygen, for example through the use of rubber surrounds.

Additionally or alternatively, to prevent the ingress of oxygen and/or moisture, in embodiments of the invention, the apparatus (including the chlorination zone) may be operated at atmospheric or superatmospheric pressure.

Additionally, or alternatively, the chlorination zone may be operated in an inert atmosphere. In other words, the environment within chlorination zone, in operation, is controlled to minimise or exclude the presence of air, and especially moisture and/or oxygen. Such control can be achieved through purging the chlorination zone and/or blanketing the chlorination zone with an inert gas, such as nitrogen.

Accordingly, in such embodiments, the oxygen content of the chlorination zone when in operation under an inert atmosphere may be below about 7000 ppm vol, below about 5000 ppm vol, below 4000 ppm vol, below 3000 ppm vol, below 2000 ppm vol, below 1000 ppm vol, below 500 ppm vol, below 250 ppm vol, below 100 ppm vol, below 50 ppm vol, below 10 ppm vol or less of oxygen.

As disclosed above, the use of chlorine comprising low levels of oxygen has been identified as an effective way to minimise the formation of problematic oxygenated organic impurities. The inventors have additionally identified that the presence of such impurities if formed can be further minimised through the use of one or more hydrolysis steps.

In such steps, reaction mixture extracted from the chlorination zone is subjected to hydrolysis, either directly (i.e. without any additional treatment steps been carried out between extraction from the chlorination zone and hydrolysis) or indirectly (i.e. following one or more treatment steps (e.g. one or more distillation steps and/or other treatment steps) carried out following extraction from the chlorination zone but prior to hydrolysis).

In embodiments in which the reaction mixture (typically a mixture comprising the alkene or alkane starting material, the chlorinated alkane product and impurities including oxygenated organic compounds) is subjected to a hydrolysis step, this typically involves contacting the reaction mixture with an aqueous medium in a hydrolysis zone. Examples of aqueous media which may be employed in the hydrolysis step include water, steam and aqueous acid.

Performance of a hydrolysis step is preferable as this reduces the content of oxygenated organic compounds present in the reaction mixture.

Once the reaction mixture has been contacted with the aqueous medium to form a mixture in the hydrolysis zone, that mixture may be subjected to one or more treatment steps. For example, components of reaction mixture (e.g. a mixture comprising the chlorinated alkane product and/or unreacted alkene or alkane starting material) can be extracted from the mixture formed in the hydrolysis zone, for example via distillation preferably under reduced pressure and/or low temperature. Such a step can be achieved while the mixture is present in the hydrolysis zone. Additionally or alternatively, the mixture may firstly be extracted from the hydrolysis zone and subjected to the extraction step remotely from that zone.

Additionally or alternatively, in embodiments of the invention, a biphasic mixture may be formed in the hydrolysis zone. In such embodiments, a phase separation step may be performed in which the organic phase comprising the chlorinated alkane is separated from the aqueous waste phase. This may be achieved by the sequential extraction of the phases from the hydrolysis zone. Alternatively, the biphasic mixture could be extracted from the hydrolysis zone and subjected to a phase separation step remote from the aqueous hydrolysis zone to extract the organic phase.

Regardless of how a mixture comprising the chlorinated alkane product is obtained following hydrolysis, the performance of the hydrolysis step will reduce the amount of oxygenated organic impurities present in that mixture. For the avoidance of doubt, where reference is made to 'a mixture comprising the chlorinated alkane' in the context of a product recovered from the hydrolysis zone, this mixture will comprise at least about 10%, at least about 20%, at least about 30%, at least about 40%, at least about 50%, at least about 60%, at least about 70%, at least about 80% or at least about 90% of the chlorinated alkane product.

The organic phase may, after optional filtering may then be subjected to distillation to obtain streams comprising purified chlorinated alkane product and/or unreacted alkene or alkane starting material. The alkene or alkane starting material may be recycled to the chlorination zone.

In embodiments of the invention in which a hydrolysis step is performed, the chlorinated alkane obtained from such a step may have an oxygenated organic compound content of about 500 ppm or less, about 200 ppm or less, about 100 ppm or less, about 75 ppm or less, about 50 ppm or less, or about 10 ppm or less, or about 5 ppm or less. Additionally or alternatively, the performance of the hydrolysis step reduces the oxygenated organic compound content of the reaction mixture by at least about 1000 ppm, at least about 800 ppm, at least about 600 ppm, at least about 500 ppm, at least about 400 ppm, at least about 300 ppm, at least about 250 ppm, at least about 200 ppm, at least about 150 ppm, at least about 100 ppm, at least about 50 ppm, at least about 25 ppm, at least about 20 ppm or at least about 10 ppm.

Additionally or alternatively, the organic phase can be subjected to additional hydrolysis steps as outlined above. The hydrolysis steps can be repeated if required, for example, one, two, three or more times.

In embodiments of the invention, the aqueous phase may be subjected to one or more treatment steps in order to reduce the organic impurity content, especially the chlorinated organic impurity content. Examples of such treatment steps that may be performed include distillation and/or steam stripping, adsorption for example on activated carbon and/or ion-exchange resins, alkaline high-temperature treatment, biological aerobic treatment or a combination thereof.

The reaction mixture obtained from the chlorination zone can be subjected to one or more distillation steps (prior to and/or following any hydrolysis steps that may be performed), preferably conducted at a temperature of about 100° C. or lower, about 90° C. or lower or about 80° C. or lower.

Such distillation steps may be conducted under vacuum. Where vacuum distillation is carried out, the vacuum conditions may be selected such that the distillation may be conducted at a low temperature and/or to facilitate the extraction of higher molecular weight chlorinated alkanes.

Any distillation equipment known to those skilled in the art can be employed in the processes of the present invention, for example a distillation boiler/column arrangement. However, it has unexpectedly been found that the formation of chlorinated alkane degradation products can be minimised if distillation apparatus formed of certain materials are avoided.

Thus in embodiments of the invention in which distillation apparatus is employed, the distillation apparatus may be free of components which, in use of the distillation apparatus, would come into contact with the process fluids (including the liquid or distillate) and comprise about 20% or more, about 10% or more, about 5% or more, about 2% or more or about 1% or more of iron.

In embodiments of the invention in which chlorinated alkane rich products are subjected to a distillation step, the distillation apparatus may be configured such that all of its components which, in use of the distillation apparatus, would come into contact with the distillate or process fluid, are produced from fluoropolymers, fluorochloropolymers, glass, enamel, phenolic resin impregnated graphite, silicium carbide and/or fluoropolymer impregnated graphite.

Where distillation step/s are performed as part of the processes of the present invention, streams obtained from such steps which have high levels of the alkene starting material may be recycled and fed into the chlorination zone.

Additional steps to minimise the formation of oxygenated organic compounds may also be obtained. For example, the chlorination zone, hydrolysis zone (if used) and/or distillation apparatus (if used) may be operated under reduced oxygen and/or moisture conditions, i.e. where the chlorination zone, hydrolysis zone (if used) and/or distillation apparatus (if used) are controlled such that the oxygen and/or moisture level is reduced as compared to the ambient atmosphere. This can be achieved by, for example, the chlorination zone, hydrolysis zone (if used) and/or distillation apparatus (if used) being operated in an inert atmosphere which may be achieved through inert gas purging and/or blanketing. The inert gas may be nitrogen.

Additionally or alternatively, apparatus upstream and/or downstream of the chlorination zone should be air-tight to prevent the ingress of oxygen and/or water, which can result in the formation of oxygenated organic impurities.

The processes of the present invention may be continuous or batch-wise.

The processes of the present invention are particularly advantageous as they enable chlorinated alkanes to be produced comprising acceptably low levels of oxygenated organic compounds using simple and straightforward techniques and equipment with which one skilled in the art would be familiar.

As can be seen from the disclosure provided herein, the inventive processes of the present invention can be operated in an integrated process, optionally in combination with other processes.

As mentioned previously, the prior art fails to disclose or teach that the presence of oxygenated organic compounds in chlorinated alkane feedstocks is problematic.

There is no teaching or disclosure in the prior art which is focused on processes for producing chlorinated alkane compounds in which the formation and presence of oxygenated organic compounds is minimised. Thus the process of the present invention is applicable to multiple types of chlorination reactions, e.g. chlorination of chlorinated alkanes to produce higher chlorinated alkanes.

In an alternative aspect of the present invention, there is provided process for producing a chlorinated alkane in which an alkene or alkane feedstock is contacted with chlorine in a chlorination zone to produce a reaction mixture containing the chlorinated alkane, wherein the chlorine supplied into the chlorination zone has an oxygen content of less than about 2000 ppmv and wherein the chlorine is chlorine gas which may be prepared by the evaporation of liquid chlorine produced by membrane or diaphragm electrolysis of sodium chloride, potassium chloride and/or hydrogen chloride.

The invention is now further illustrated in the following examples. In those examples, the following are used:

113-TCPe=1,1,3-Trichloropropene

23-DCPC=2,3-Dichloropropanoyl chloride

1133-TeCPe=1,1,3,3-Tetrachloropropene

11133-TCPa=1,1,1,3,3-Pentachloropropane

11123-PCPa=1,1,1,2,3-Pentachloropropane

111233-HCPa=1,1,1,2,3,3-Hexachloropropane

111223-HCPa=1,1,1,2,2,3-Hexachloropropane

Example 1: Chlorination Using Visible Light Irradiation, Under Nitrogen

Chlorination

A batch operated reactor consisting of a four neck Simax™ glass flask equipped with a stirrer, thermometer, back cooler, feed and discharge neck, neck for nitrogen introduction and cooling jacket was set up. The reactor was equipped with a 400 W high pressure Hg external lamp with a luminescence layer type RVLX400 producing mainly visible spectrum. The feedstock consisted of pure 1,1,3-trichloropropene which was freshly distilled just before the experiment, and its quality analyzed by GC and handled under nitrogen. Minor amounts of HCl gas were formed and these together with traces of chlorine were cooled down by means of a back cooler/condenser and then absorbed in a caustic soda scrubber. Gaseous chlorine was evaporated from liquid chlorine from the cylinder of quality 2.8 (supplier Linde Gas, 99.8% vol), and was introduced into the liquid reaction mixture via a dip pipe in amount equal to 80% of theoretical based on the trichloropropene feedstock for a period of 70 minutes. Nitrogen blanketing was introduced in a controlled measured mode into the reactor prior and maintained during the reaction, sampling and water treatment. The temperature of reaction was maintained at 30 to 34° C. Pressure was atmospheric. The chlorine was totally consumed during the reaction. A sample of the reaction mixture was dissolved at 1:1 wt ratio in an inert solvent (tetrachloromethane) with phenol-based stabilizer and the mixture was analyzed by gas chromatography (GC).

Hydrolysis

Then hot water was added in an amount of 35 wt. % based on the weight of reaction mixture and the resulting liquid system was stirred for another 30 min. while the temperature dropped from initially 44 to 34° C. After stopping stirring, two liquid layers separated and samples from each layer were taken. The sample of the reaction mixture (organic bottom layer) was dissolved in the inert solvent with phenol-based stabilizer and analyzed by GC and the results are shown in Table 1 (without the solvent):

TABLE 1

| Example 1 | Feedstock (%) | After chlorination (%) | After hydrolysis (%) |
|---|---|---|---|
| 113-TCPe | 99.907 | 15.641 | 15.456 |
| 23-DCPC |  | 0.0172 | 0.0063 |
| 1133-TeCPe | 0.005 | 0.714 | 0.746 |
| 11123-PCPa | 0.005 | 82.105 | 82.082 |
| 111233-HCPa |  | 1.076 | 1.051 |
| 111223-HCPa |  | 0.088 | 0.086 |

As can be seen, the chlorination resulted in over 82% of the target product (1,1,1,2,3-pentachloropropane) being obtained. Chlorination also resulted in the formation of 0.0172% of 2,3-dichloropropanoyl chloride (23-DCPC), an oxygenated organic impurity. The hydrolysis step further reduced the content of that impurity to 0.0063%

Example 2: Chlorination Using Visible Light Irradiation, Under Nitrogen, with Added Oxygen from Air Chlorination A batch operated reactor comprising a four neck Simax™ glass flask equipped with a stirrer, thermometer, back cooler, feed and discharge neck, neck for nitrogen introduction and cooling jacket was set up. The reactor was equipped as in Example 1 with a 400 W high pressure Hg external lamp type RVLX400 producing mainly visible spectrum. The feedstock consisted of pure 1,1,3-trichloropropene which was freshly distilled just before the experiment, and its quality analyzed by GC and handled under nitrogen. Minor amounts of HCl gas were formed and these together with traces of chlorine were cooled down by means of a back cooler/condenser and then absorbed in a caustic soda scrubber.

As in Example 1, gaseous chlorine from the cylinder of quality 2.8 (supplier Linde Gas) was introduced into the liquid reaction mixture via a dip pipe in amount equal to 80% of theoretical based on the trichloropropene feedstock for 72 minutes.

There was also introduced pressurized air in a controlled measured mode into the same chlorine gas dip pipe—i.e. the chlorine was mixed with air before it reached the reaction mixture via dip pipe. The amount of air introduced was set up in order to reach 0.75% vol. of oxygen in the chlorine gas after mixing. Nitrogen blanketing was introduced in a controlled measured mode into the reactor prior and maintained during the reaction, sampling and water treatment. The temperature of reaction was maintained at 23 to 30° C. Pressure was atmospheric. The chlorine was totally consumed during the reaction. A sample of the reaction mixture was dissolved in an inert solvent (tetrachloromethane) with phenol-based stabilizer and the mixture was analyzed by gas chromatography.

Hydrolysis

Hot water was added [amount of 35 wt. % towards amount of reaction mixture] and the resulting liquid system was stirred for another 30 min. while the temperature dropped from initially 44° C. to 34° C. After stopping the stirring, two liquid layers separated and samples from each layer were taken. The sample of the reaction mixture (organic bottom layer) was dissolved in the inert solvent with phenol-based stabilizer and analyzed by GC and the results are shown in Table 2 (without solvent).

TABLE 2

| Example 2 | Feedstock (%) | After chlorination (%) | After hydrolysis (%) |
|---|---|---|---|
| 113-TCPe | 99.91 | 13.21 | 12.39 |
| 23-DCPC |  | 0.3635 | 0.0509 |
| 1133-TeCPe | 0.01 | 0.67 | 0.69 |
| 11123-PCPa | 0.00 | 84.32 | 85.29 |
| 111233-HCPa |  | 1.17 | 1.18 |
| 111223-HCPa |  | 0.10 | 0.10 |

As is apparent from comparing the results in Table 1 and Table 2, the amount of oxygenated organic compound 2,3-dichloropropanoyl chloride (23-DCPC) produced during chlorination was substantially higher when a chlorine containing significant amounts of oxygen was fed into the chlorination zone.

As with other acid chlorides, 2,3-dichloropropanoyl chloride is not stable in the presence of moisture and can form corresponding acids which can lead to further corrosion or contamination issues, such as corrosion of reaction vessels, interlinking pipes, joints, distillation units and water treatment units. Such acids are also difficult to remove by distillation.

Example 3: Chlorination Using UV-Light Irradiation, Under Nitrogen

Chlorination

A batch operated reactor consisting of a four neck Simax™ glass flask equipped with a stirrer, thermometer, back cooler, feed and discharge neck, neck for nitrogen introduction and cooling jacket was set up. The reactor was equipped with a 125 W high pressure Hg internal lamp HPL 125 in immersed quartz-glass tube. The feedstock consisted of pure 1,1,3-trichloropropene which was freshly distilled just before the experiment, and its quality analyzed by GC and handled under nitrogen. Minor amounts of HCl gas were formed and these together with traces of chlorine were cooled down by means of a back cooler/condenser and then absorbed in a caustic soda scrubber. Gaseous chlorine was evaporated from liquid chlorine from the cylinder of quality 2.8 (supplier Linde Gas, 99.8% vol.), and was introduced into the liquid reaction mixture via a dip pipe in amount equal to 80% of theoretical based on the trichloropropene feedstock for a period of 97 minutes. Nitrogen blanketing was introduced in a controlled measured mode into the reactor prior and maintained during the reaction, sampling and water treatment. The temperature of reaction was maintained at 29 to 30° C. Pressure was atmospheric. The chlorine was totally consumed during the reaction. A sample of the reaction mixture was dissolved at 1:1 wt ratio in an inert solvent (tetrachloromethane) with phenol-based stabilizer and the mixture was analyzed by gas chromatography.

Hydrolysis

Then water was added in an amount of 37 wt. % based on the weight of reaction mixture and the resulting liquid system was stirred for another 60 min. While the temperature was 23° C. After stopping stirring, two liquid layers separated and samples from each layer were taken. The sample of the reaction mixture (organic bottom layer) was dissolved in the inert solvent with phenol-based stabilizer and analyzed by GC and the results are shown in Table 3 (without the solvent):

TABLE 3

| Example 3 | Feedstock (%) | After chlorination (%) | After hydrolysis (%) |
|---|---|---|---|
| 113-TCPe | 99.841 | 13.922 | 13.919 |
| 23-DCPC |  | 0.0198 | 0.0081 |
| 1133-TeCPe | 0.015 | 0.722 | 0.726 |
| 11123-PCPa | 0.022 | 83.471 | 83.518 |
| 111233-HCPa |  | 1.095 | 1.111 |
| 111223-HCPa |  | 0.090 | 0.092 |

As can be seen, the chlorination resulted in over 83% of the target product (1,1,1,2,3-pentachloropropane) being obtained. Chlorination also resulted in the formation of 0.0198% of 2,3-dichloropropanoyl chloride (23-DCPC), an oxygenated organic impurity. The hydrolysis step further reduced the content of that impurity to 0.0081%

Example 4: Chlorination Using UV-Light Irradiation, Under Nitrogen, with Added Oxygen from Air Chlorination A batch operated reactor comprising a four neck Simax™ glass flask equipped with a stirrer, thermometer, back cooler, feed and discharge neck, neck for nitrogen introduction and cooling jacket was set up. The reactor was equipped with a 125 W high pressure Hg internal lamp HPL 125 in immersed quartz-glass tube. The feedstock consisted of pure 1,1,3-trichloropropene which was freshly distilled just before the experiment, and its quality analyzed by GC and handled under nitrogen. Minor amounts of HCl gas were formed and these together with traces of chlorine were cooled down by means of a back cooler/condenser and then absorbed in a caustic soda scrubber.

As in Example 1, gaseous chlorine from the cylinder of quality 2.8 (supplier Linde Gas) was introduced into the liquid reaction mixture via a dip pipe in amount equal to 80% of theoretical based on the trichloropropene feedstock for 101 minutes.

There was also introduced pressurized air in a controlled measured mode into the same chlorine gas dip pipe—i.e. the chlorine was mixed with air before it reached the reaction mixture via dip pipe. The amount of air introduced was set up in order to reach 0.79% vol. of oxygen in the chlorine gas after mixing. Nitrogen blanketing was introduced in a controlled measured mode into the reactor prior and maintained during the reaction, sampling and water treatment. The temperature of reaction was maintained at 29 to 31° C. Pressure was atmospheric. The chlorine was totally consumed during the reaction. A sample of the reaction mixture was dissolved in an inert solvent (tetrachloromethane) with phenol-based stabilizer and the mixture was analyzed by gas chromatography.

Hydrolysis

Water was added [amount of 36 wt. % towards amount of reaction mixture] and the resulting liquid system was stirred for another 60 min. while the temperature was 23° C. After stopping the stirring, two liquid layers separated and samples from each layer were taken. The sample of the reaction mixture (organic bottom layer) was dissolved in the inert solvent with phenol-based stabilizer and analyzed by GC and the results are shown in Table 4 (without solvent).

TABLE 4

| Example 4 | Feedstock (%) | After chlorination (%) | After hydrolysis (%) |
|---|---|---|---|
| 113-TCPe | 99.841 | 14.230 | 14.796 |
| 23-DCPC |  | 0.1730 | 0.0505 |
| 1133-TeCPe | 0.015 | 0.756 | 0.783 |
| 11123-PCPa | 0.022 | 83.134 | 82.703 |
| 111233-HCPa |  | 1.149 | 1.130 |
| 111223-HCPa |  | 0.093 | 0.089 |

As is apparent from comparing the results in Table 3 and Table 4, the amount of oxygenated organic compound 2,3-dichloropropanoyl chloride (23-DCPC) produced during chlorination was substantially higher when a chlorine containing significant amounts of oxygen was fed into the chlorination zone.

As with other acid chlorides, 2,3-dichloropropanoyl chloride is not stable in the presence of moisture and can form corresponding acids which can lead to further corrosion or contamination issues, such as corrosion of reaction vessels, interlinking pipes, joints, distillation units and water treatment units. Such acids are also difficult to remove by distillation.

Example 5: Effect of Oxygen on the Formation of 2,3-Dichloropropanoyl Chloride During Chlorination of 1,1,3-Trichloropropene Using Gaseous Chlorine Evaporated from Liquid Chlorine A batch operated reactor consisting of a four neck Simax™ glass flask equipped with a stirrer, thermometer, back cooler, feed and discharge neck, neck for nitrogen introduction and cooling jacket was set up. The reaction mixture was exposed to day light. Off gases were absorbed by means of an absorption column located downstream of the condenser. The feedstock used (996 g of pure 1,1,3-trichloropropene) was washed by water and dried immediately prior to commencement of the experiment, and its quality analyzed by GC and handled under nitrogen. Traces of HCl gas were formed during the reaction and these together with traces of chlorine were cooled down by means' of a back cooler/condenser and then absorbed in a caustic soda scrubber. Gaseous chlorine which contained 0.025% mol. of oxygen was evaporated from steel cylinder containing liquid chlorine and was introduced into the liquid reaction mixture via a dip pipe for 124-125 minutes. Nitrogen blanketing was introduced in a controlled measured mode into the reactor prior to commencement of the reaction and then maintained during the reaction and sampling. The temperature of reaction was maintained at 25° C. Pressure was atmospheric.

Samples of the reaction mixture were taken at different times according to the reaction progress and were dissolved in an inert solvent (tetrachloromethane) with a phenol-based stabilizer and the resulting mixtures were analyzed by GC. The results (GC figures without solvent) are shown in Table 5.

TABLE 5

| Example 5 | Feedstock | Ex. 5.1 | Ex. 5.2 | Ex. 5.3 | Ex. 5.4 | Ex. 5.5 |
|---|---|---|---|---|---|---|
| Chlorine (mol % per 113-TCPe feed) | 0.0 | 30.5 | 61.0 | 76.0 | 91.3 | 101.9 |
| Oxygen (mol % per 113-TCPe feed) | 0.00 | 0.008 | 0.015 | 0.019 | 0.023 | 0.025 |
| Concentration of $O_2$ in $Cl_2$ gas feed (mol %) | | 0.025 | 0.025 | 0.025 | 0.025 | 0.025 |
| DCPC (mol/h per 1000 g 113-TCPe feed) | | 0.12 | 0.10 | 0.10 | 0.10 | 0.10 |
| DCPC/O yield (%) | | 67.2 | 57.0 | 58.9 | 57.1 | 62.4 |
| GC analysis (%) | | | | | | |
| 113-TCPe | 98.540 | 63.026 | 33.268 | 20.150 | 8.474 | 1.217 |
| 23-DCPC | 0.005 | 0.014 | 0.019 | 0.022 | 0.024 | 0.027 |
| 1133-TeCPe | 0.441 | 0.897 | 1.023 | 0.926 | 0.660 | 0.224 |
| 11123-PCPa | 0.429 | 35.238 | 64.405 | 77.181 | 88.513 | 95.218 |
| 111233-HCPa | 0.001 | 0.218 | 0.681 | 1.068 | 1.677 | 2.527 |

As can be seen, chlorination of the starting alkene in an environment with low levels of oxygen present resulted in the formation of acceptably low levels of dichloropropanoyl chloride.

Example 6: Effect of Oxygen on the Formation of 2,3-Dichloropropanoyl Chloride During Chlorination of 1,1,3-Trichloropropene Using Chlorine Quality of Membrane Electrolysis The process of Example 5 was repeated using the same equipment, temperature and pressure. Gaseous chlorine with an oxygen content of about 0.5% by volume, (which is typical of chlorine gas obtained via chlor-alkali membrane electrolysis processes) was used instead of chlorine with low oxygen content. Air was introduced into the chlorine in a controlled measured mode—i.e. the chlorine was mixed with air before introduction into reaction mixture via a dip pipe. The amount of air introduced was controlled to facilitate the attainment of an oxygen level of 0.54% mol. in the chlorine gas. The target level of 0.54% mol. was selected as this corresponds to the oxygen content in membrane grade dry chlorine (before compression). The amount of 1,1,3-trichloropropene feed treated according to Example 5 was 1024 g.

Samples of the reaction mixture were taken at different time according to reaction progress and were dissolved in an inert solvent (tetrachloromethane) with phenol-based stabilizer and the resulting mixtures were analyzed by GC. The results (GC figures without solvent) are shown in Table 6.

TABLE 6

| Example 6 | Feedstock | Ex. 6.1 | Ex. 6.2 | Ex. 6.3 | Ex. 6.4 | Ex. 6.5 |
|---|---|---|---|---|---|---|
| Chlorine (mol % per 113-TCPe feed) | 0.0 | 30.4 | 60.9 | 76.1 | 91.3 | 101.5 |
| Oxygen (mol % per 113-TCPe feed) | 0.00 | 0.17 | 0.34 | 0.42 | 0.50 | 0.56 |
| Concentration of $O_2$ in $Cl_2$ gas feed (mol %) | | 0.57 | 0.55 | 0.55 | 0.55 | 0.55 |
| DCPC (mol/h per 1000 g 113-TCPe feed) | | 1.82 | 2.19 | 2.30 | 2.22 | 2.14 |
| DCPC/O yield (%) | | 48.0 | 59.5 | 62.2 | 60.9 | 58.9 |
| GC analysis (%) | | | | | | |
| 113-TCPe | 98.589 | 63.291 | 33.080 | 20.108 | 8.259 | 1.472 |
| 23-DCPC | 0.006 | 0.163 | 0.342 | 0.421 | 0.469 | 0.488 |
| 1133-TeCPe | 0.425 | 0.884 | 1.022 | 0.934 | 0.652 | 0.247 |
| 11123-PCPa | 0.402 | 34.793 | 64.270 | 76.860 | 88.266 | 94.598 |
| 111233-HCPa | 0.001 | 0.213 | 0.676 | 1.061 | 1.671 | 2.410 |

As can be seen, chlorination in the presence of increased oxygen content resulted in the formation of significantly higher amounts of dichloropropanoyl chloride. With higher reaction progress/conversion of starting material there is also increased amount of the organic oxygenated impurity DCPC and also higher amounts of the heavies 111233-HCPa and 111223-HCPa.

Example 7: Oxidation of 1,1,3-Trichloropropene—Effect of Oxygen on the Formation of 2,3-Dichloropropanoyl Chloride The process was carried out as described in Example 6 above using same amount of oxygen with same reaction time (which corresponded to chlorination using membrane chlorine) but without introduction of chlorine into the liquid reaction mixture. Thus only the oxidation of 1,1,3-trichloropropene feedstock using pressurized air took place. The amount of 1,1,3-trichloropropene feed treated according to Example 5 was 1073 g.

Samples of the reaction mixture were taken at different time according to reaction progress and were dissolved in an inert solvent (tetrachloromethane) with phenol-based stabilizer and the resulting mixtures were analyzed by GC. The results (GC figures without solvent) are shown in Table 7.

chlorination using membrane chlorine) and the same partial pressure of oxygen being used in the gaseous feedstock compared to chlorination in Example 6 (oxygen in air was further diluted by nitrogen to get the same partial pressure in gaseous feedstock as in Example 6). Thus only oxidation of the 1,1,3-trichloropropene feedstock using a mixture of oxygen and nitrogen took place. The amount of 1,1,3-trichloropropene feed treated according to Example 5 was 807 g.

Samples of the reaction mixture were taken at different time according to reaction progress and were dissolved in an inert solvent (tetrachloromethane) with phenol-based stabilizer and the resulting mixtures were analyzed by GC. The results (GC figures without solvent) are shown in Table 8.

TABLE 8

| Example 8 | Feedstock | Ex. 8.1 | Ex. 8.2 | Ex. 8.3 | Ex. 8.4 | Ex. 8.5 |
|---|---|---|---|---|---|---|
| Chlorine (mol % per 113-TCPe feed) | 0.0 | 0.0 | 0.0 | 0.0 | 0.0 | 0.0 |
| Oxygen (mol % per 113-TCPe feed) | 0.00 | 0.20 | 0.32 | 0.40 | 0.48 | 0.54 |
| Concentration of $O_2$ in gas feed (mol %) | | 0.59 | 0.59 | 0.59 | 0.59 | 0.59 |
| DCPC (mol/h per 1000 g 113-TCPe feed) | | 0.44 | 0.43 | 0.46 | 0.50 | 0.49 |
| DCPC/O yield (%) | | 12.1 | 12.3 | 13.4 | 14.1 | 13.4 |
| GC analysis (%) | | | | | | |
| 113-TCPe | 98.490 | 98.404 | 98.361 | 98.296 | 98.261 | 98.314 |
| 23-DCPC | 0.017 | 0.069 | 0.102 | 0.135 | 0.166 | 0.177 |
| 1133-TeCPe | 0.436 | 0.440 | 0.444 | 0.447 | 0.449 | 0.442 |
| 11123-PCPa | 0.424 | 0.459 | 0.443 | 0.443 | 0.445 | 0.424 |
| 111233-HCPa | 0.002 | 0.002 | 0.002 | 0.002 | 0.002 | 0.002 |

TABLE 7

| | Feedstock | Ex. 7.1 | Ex. 7.2 | Ex. 7.3 | Ex. 7.4 |
|---|---|---|---|---|---|
| Chlorine (mol % per 113-TCPe feed) | 0.0 | 0.0 | 0.0 | 0.0 | 0.0 |
| Oxygen (mol % per 113-TCPe feed) | 0.00 | 0.17 | 0.32 | 0.40 | 0.48 |
| Concentration of $O_2$ in gas feed (mol %) | | 20.95 | 20.95 | 20.95 | 20.95 |
| DCPC (mol/h per 1000 g 113-TCPe feed) | | 0.67 | 0.78 | 0.80 | 0.83 |
| DCPC/O yield (%) | | 20.0 | 22.5 | 22.4 | 23.7 |
| GC analysis (%) | | | | | |
| 113-TCPe | 98.562 | 98.424 | 98.320 | 98.321 | 98.230 |
| 23-DCPC | 0.009 | 0.081 | 0.167 | 0.206 | 0.258 |
| 1133-TeCPe | 0.439 | 0.434 | 0.440 | 0.435 | 0.445 |
| 11123-PCPa | 0.414 | 0.415 | 0.426 | 0.419 | 0.435 |
| 111233-HCPa | | | 0.002 | 0.002 | |

As can be seen, where oxidation of 1,1,3-trichloropropene occurs in the absence of chlorination, the formation of dichloropropanoyl chloride is significantly reduced.

Example 8: Oxidation of 1,1,3-Trichloropropene—Effect of Oxygen on the Formation of 2,3-Dichloropropanoyl Chloride The process was carried out as described in Example 7 above, with the same reaction time (corresponding to the As can be seen, oxidation alone, without chlorination, using the same partial pressure of oxygen in the gaseous feedstock compared to Example 6 results in the formation of much lower amounts of dichloropropanoyl chloride. It has been found that, surprisingly, chlorine appears to promote an increased rate of reaction between the oxygen molecule and the alkene organic substrate, i.e. there is an increased rate of formation of the organic oxygenated compound. Thus the oxygen content in chlorine as the gaseous feedstock for chlorination of the organic molecule (substrate) is a critical parameter because chlorine is found to be a promoter of the oxidation reaction and the undesired oxygenated by-products, are formed to a greater extent.

Example 9: Oxidation of 1,1,3-Trichloropropene—Effect of Only Oxygen on the Formation of 2,3-Dichloropropanoyl Chloride A batch operated reactor consisting of a four neck Simax™ glass flask equipped with a stirrer, thermometer, back cooler, feed and discharge neck, neck for nitrogen introduction and cooling jacket was set up. The reaction mixture was exposed to daylight. Off gases were absorbed by means of an absorption column located downstream of the condenser. The feedstock (805 g of pure 1,1,3-trichloropropene) was washed by water and dried immediately prior to commencement of the experiment, and its quality analyzed by GC and handled under nitrogen. The gaseous feedstock (air) was fed into the reactor at a rate of 35.4 $Ndm^3$/hour for 6 hours in total.

Nitrogen blanketing was introduced in a controlled measured mode into the reactor prior to and during the reaction and sampling. The temperature of reaction was maintained at 30° C. Pressure was atmospheric.

Samples of the reaction mixture were taken every two hours following commencement of the reaction and were dissolved in an inert solvent (tetrachloromethane) with phenol-based stabilizer. The resulting mixture was analyzed by GC. The results (GC figures without solvent) are shown in Table 9.

TABLE 9

| | Example 9 | | | |
|---|---|---|---|---|
| | Feedstock | Ex. 9.1 | Ex. 9.2 | Ex. 9.3 |
| | | Time (hours) | | |
| | 0:00 | 2:00 | 4:00 | 6:00 |
| Oxygen (mol % per 113-TCPe feed) | 0.0 | 10.6 | 21.2 | 31.9 |
| Chlorine (mol % per 113-TCPe feed) | 0.0 | 0.0 | 0.0 | 0.0 |
| DCPC (mol/h per 1000 g 113-TCPe feed) | | 1.01 | 1.69 | 1.97 |
| DCPC/O yield (%) | | 1.39 | 2.31 | 2.70 |
| GC analysis (%) | | | | |
| 113-TCPe | 99.787 | 99.031 | 97.943 | 96.734 |
| 23-DCPC | 0.004 | 0.331 | 1.090 | 1.902 |
| 1133-TeCPe | 0.001 | 0.001 | 0.001 | 0.001 |
| 11123-PCPa | 0.004 | 0.007 | 0.018 | 0.019 |
| 111233-HCPa | 0.000 | 0.000 | 0.000 | 0.000 |
| 111223-HCPa | 0.000 | 0.000 | 0.000 | 0.000 |

As can be seen, oxidation of the starting material in the absence of chlorine at 30° C. over a period of 6 hours resulted in the formation of limited amounts of dichloropropanoyl chloride.

Example 10: Oxidation of
1,1,3-Trichloropropene—Effect of Presence of
Chlorine in Oxygen on the Formation of
2,3-Dichloropropanoyl Chloride The process was carried out as described in Example 9 above, with the same reaction time and temperature and the same amount of air. A small amount of chlorine was added into the air feed stream. The feedstock used (805 g of pure 1,1,3-trichloropropene) was washed by water and dried immediately prior to commencement of the experiment. Its quality was analyzed by GC and it was handled under nitrogen.

The gaseous feedstock (air and chlorine provided at respective rates of 35.4 Ndm³/hour of air and 6 g/hour of chlorine) was fed into the reactor for 6 hours in total.

Samples of the reaction mixture were taken every two hours following commencement of the reaction and were dissolved in an inert solvent (tetrachloromethane) with phenol-based stabilizer. The resulting mixture was analyzed by GC. The results (GC figures without solvent) are shown in Table 10.

TABLE 10

| | Example 10 | | | |
|---|---|---|---|---|
| | Feedstock | Ex. 10.1 | Ex. 10.2 | Ex. 10.3 |
| | | Time (hours) | | |
| | 0:00 | 2:00 | 4:00 | 6:00 |
| Oxygen (mol % per 113-TCPe feed) | 0.0 | 10.6 | 21.3 | 31.9 |
| Chlorine (mol % per 113-TCPe feed) | 0.0 | 3.1 | 6.4 | 9.4 |
| DCPC (mol/h per 1000 g 113-TCPe feed) | | 27.08 | 26.14 | 27.91 |
| DCPC/O yield (%) | | 37.1 | 35.8 | 38.2 |
| GC analysis (%) | | | | |
| 113-TCPe | 99.808 | 86.873 | 74.304 | 62.690 |
| 23-DCPC | 0.004 | 8.486 | 15.883 | 24.707 |
| 1133-TeCPe | 0.001 | 0.239 | 0.469 | 0.657 |
| 11123-PCPa | 0.005 | 2.799 | 5.540 | 7.818 |
| 111233-HCPa | | 0.004 | 0.010 | 0.018 |

As, can be seen, in an oxidation process carried out in the same way as Example 9, the presence of gaseous chlorine and oxygen, resulting in a 14-fold increase in the yield of the oxygenated organic compound dichloropropanoyl chloride.

It therefore appears that, surprisingly, chlorine is promoting the reaction between molecular oxygen and the organic substrate, i.e. chlorine promotes the rate of substrate oxidation, and thus the rate of formation of the organic oxygenated to compound.

Accordingly, it has been found that avoiding the use of a combination of oxygen and chlorine in the gaseous feedstock for chlorination of the organic starting material is critical, because chlorine appears to be a potent promoter of oxidation reactions and significantly increases the formation of unwanted oxygenated by-products.

Example 11 Oxidation of
1,1,1,3-Tetrachloropropane—Effect of Low Oxygen
in Chlorine on the Formation of
2,3-Dichloropropanoyl Chloride A batch operated reactor consisting of a four neck Simax™ glass flask equipped with a stirrer, back cooler, feed and discharge neck, thermometer neck combined with nitrogen blanketing introduction and cooling jacket was set up. There was also inserted a quartz sleeve tube with 125 W high pressure Hg lamp for UV introduction. Off gases were absorbed by means of an absorption column located downstream of the condenser. The feedstock used consisted of pure 1,1,1,3-tetrachloropropane in amount of 1050 g (quality analyzed by GC) and handled under nitrogen. HCl gas was formed during reaction and that together with traces of chlorine were cooled down by means of a back cooler/condenser and then absorbed in a caustic soda scrubber.

The gaseous feedstock consists of only the evaporated gas from liquid chlorine from a cylinder and this gas was introduced into the liquid reaction mixture using a dip-pipe.

Nitrogen blanketing was introduced in a controlled measured mode into the reactor prior to the chlorine introduction and maintained during the reaction and sampling. The temperature of reaction was maintained at 25° C. Pressure was atmospheric. Samples of the reaction mixture were taken each approx. 23 min. intervals (which equates to adding 10% of theoretical amount of chlorine at intervals) and the mixture was analyzed by GC. There was no stabilization of the sample as it is sufficiently stable under the ambient conditions. The results are shown in Table 11.

TABLE 11

| | Feedstock | Example 11 | | | |
| --- | --- | --- | --- | --- | --- |
| | | 11.1 | 11.2 | 11.3 | 11.4 |
| Chlorine (mol % per 1113-TeCPa feed) | | 10.0 | 20.0 | 30.0 | 39.9 |
| Oxygen (mol % per 1113-TeCPa feed) | | 0.002 | 0.005 | 0.007 | 0.010 |
| Concentration of $O_2$ in $Cl_2$ gas feed (mol %) | | 0.025 | 0.025 | 0.025 | 0.025 |
| DCPC/O yield (%) | | 57.6 | 42.3 | 36.7 | 33.5 |
| GC analysis (%) | | | | | |
| 23-DCPC | | 0.003 | 0.004 | 0.005 | 0.006 |
| 1113-TeCPa | 99.947 | 89.966 | 79.627 | 69.394 | 59.467 |
| 11133-PCPa | 0.001 | 7.824 | 15.857 | 23.727 | 31.236 |
| 11123-PCPa | 0.000 | 2.059 | 4.159 | 6.196 | 8.090 |
| 111333-HCPa | | 0.026 | 0.106 | 0.252 | 0.486 |
| 111233-HCPa | | 0.023 | 0.088 | 0.198 | 0.380 |
| 111223-HCPa | | 0.012 | 0.048 | 0.112 | 0.216 |

As can be seen, UV chlorination of alkane using chlorine with limited amount of oxygen at 25° C. during 1:30 hour results in formation of limited amount (30-60 ppm) of 2,3-dichloropropanoyl chloride.

Example 12: Oxidation of 1,1,1,3-Tetrachloropropane—Effect of High Oxygen in Chlorine Content on the Formation of 2,3-Dichloropropanoyl Chloride The process was carried out as described in Example 11, with the same reaction time, temperature and amount of tetrachloropropane feedstock, but chlorine was mixed with air to increase the content of oxygen to some 0.5% vol and this gaseous feed stream was introduced into the reactor using the dip pipe.

Samples of the reaction mixture were taken each approx. 23 min intervals (which equates to adding 10% of theoretical amount of chlorine at intervals) and the mixture was analyzed by GC. There was no stabilization of the sample as it is sufficiently stable under the ambient conditions. The results are shown in Table 12.

TABLE 12

| | Feedstock | Example 12 | | | |
| --- | --- | --- | --- | --- | --- |
| | | 12.1 | 12.2 | 12.3 | 12.4 |
| Chlorine (mol % per 1113-TeCPa feed) | | 9.5 | 20.0 | 29.7 | 40.0 |
| Oxygen (mol % per 1113-TeCPa feed) | | 0.05 | 0.10 | 0.15 | 0.21 |
| Concentration of $O_2$ in $Cl_2$ gas feed (mol %) | | 0.51 | 0.52 | 0.52 | 0.52 |
| DCPC/O yield (%) | | 40.7 | 35.5 | 32.5 | 31.9 |
| GC analysis (%) | | | | | |
| 23-DCPC | | 0.035 | 0.063 | 0.084 | 0.109 |
| 1113-TeCPa | 99.947 | 90.416 | 79.669 | 69.582 | 59.447 |
| 11133-PCPa | 0.002 | 7.495 | 15.891 | 23.649 | 31.316 |
| 11123-PCPa | 0.001 | 1.938 | 4.067 | 6.027 | 7.920 |
| 111333-HCPa | | 0.023 | 0.103 | 0.246 | 0.483 |
| 111233-HCPa | | 0.020 | 0.081 | 0.193 | 0.369 |
| 111223-HCPa | | 0.009 | 0.041 | 0.100 | 0.193 |

As can be seen, the presence of increased amount of oxygen in chlorine during the alkane chlorination results in the formation of a much higher amount of the product of oxidation, namely 2,3-dichloropropanoyl chloride.

Such 0.5% vol. of oxygen in chlorine approximates the oxygen content in the dry chlorine leaving the membrane chloro-alkali plant before chlorine liquefaction.

Thus, surprisingly, the oxygen in chlorine can also form oxygenated organic compounds, such as propanoyl chlorides during the chlorination of saturated alkane molecule, particularly chlorinated alkanes. Hence, the combination oxygen and chlorine, i.e. content of oxygen in chlorine, in the gaseous feedstock for chlorination of organic both alkene and alkane molecule (substrate) is critical parameter because chlorine is even promoter of oxidation reaction and oxygenated by-products are formed in a great extent.

The invention claimed is:

1. An industrial process for producing a $C_{3-6}$ chlorinated alkane in which a chlorinated alkene or a chlorinated alkane feedstock is contacted with chlorine in a chlorination zone to produce a reaction mixture containing the $C_{3-6}$ chlorinated alkane, wherein the chlorine supplied into the chlorination zone has a dissolved oxygen content of less than about 2000ppmv and wherein:
    the chlorination zone is closed to the atmosphere, and/or
    the chlorination zone is operated under atmospheric or superatmospheric pressure, and/or
    the chlorination zone is operated under an inert atmosphere, and/or
    the dissolved oxygen content in the chlorinated alkene or chlorinated alkane feedstock is less than 2000 ppm,
and wherein
the reaction mixture is extracted from the chlorination zone and comprises oxygenated organic compounds in amounts of about 500 ppm or less, about 250 ppm or less, about 100 ppm or less, about 50 ppm or less, about 10 ppm or less, or about 5 ppm or less.

2. The process of claim 1, wherein reaction mixture is extracted from the chlorination zone and is subjected to a hydrolysis step.

3. The process according to claim 2, wherein the hydrolysis step comprises contacting the reaction mixture with an aqueous medium in a hydrolysis zone.

4. The process according to claim 3, wherein the aqueous medium is acidic.

5. The process according to claim 3, further comprising a step of extracting a mixture comprising the $C_{3-6}$ chlorinated alkane from the hydrolysis zone.

6. The process according to claim 5, wherein the reaction mixture comprising the $C_{3-6}$ chlorinated alkane comprises oxygenated organic compounds in amounts of about 500 ppm or less, about 250 ppm or less, about 100 ppm or less, about 50 ppm or less, about 10 ppm or less, or about 5 ppm or less.

7. The process of claim 1, wherein reaction mixture extracted from the chlorination zone is subjected to one or more distillation steps.

8. The process of claim 7, wherein at least one distillation step is carried out prior to a hydrolysis step.

9. The process of claim 7, wherein at least one distillation step is carried out following a hydrolysis step.

10. The process of claim 7, wherein at least one of the distillation steps are conducted at a temperature of about 100° C. or lower.

11. The process of claim 7, wherein at least one of the distillation steps are conducted at a temperature of about 80° C. or lower.

12. The process of claim 2, comprising purging and/or blanketing the distillation apparatus and/or hydrolysis zone with an inert gas.

13. The process of claim 1, comprising purging and/or blanketing the chlorination zone with an inert gas.

14. The process of claim 12, wherein the inert gas is nitrogen.

15. A process for minimising oxygenated chlorinated compounds when producing a $C_{3-6}$ chlorinated alkane in which a $C_{3-6}$ alkene or alkane feedstock is contacted with chlorine in a chlorination zone to produce a reaction mixture containing the $C_{3-6}$ chlorinated alkane, wherein the chlorine supplied into the chlorination zone has an oxygen content of less than about 2000ppmv and wherein:
- the chlorination zone is closed to the atmosphere, and/or
- the chlorination zone is operated under atmospheric or superatmospheric pressure, and/or
- the chlorination zone is operated under an inert atmosphere, and/or
- the content of dissolved oxygen in the alkene feedstock is less than 2000 ppm.

* * * * *